(12) United States Patent
Gehrke et al.

(10) Patent No.: US 11,419,554 B2
(45) Date of Patent: Aug. 23, 2022

(54) SLEEPING OR RECLINING FURNITURE AND ELECTRIC MOTOR FURNITURE DRIVE FOR SUCH FURNITURE

(71) Applicant: DEWERTOKIN GMBH, Kirchlengern (DE)

(72) Inventors: Karsten Gehrke, Porta Westfalica (DE); Armin Hille, Bielefeld (DE); Steffen Loley, Osnabrück (DE); Alexander Tews, Bielefeld (DE)

(73) Assignee: Dewertokin Technology Group Co., Ltd, Jiaxing (CN)

( * ) Notice: Subject to any disclaimer, the term of this patent is extended or adjusted under 35 U.S.C. 154(b) by 1001 days.

(21) Appl. No.: 16/067,510

(22) PCT Filed: Dec. 30, 2016

(86) PCT No.: PCT/EP2016/082911
§ 371 (c)(1),
(2) Date: Jun. 29, 2018

(87) PCT Pub. No.: WO2017/114945
PCT Pub. Date: Jul. 6, 2017

(65) Prior Publication Data
US 2019/0008284 A1    Jan. 10, 2019

(30) Foreign Application Priority Data

Dec. 30, 2015 (DE) .................... 20 2015 107 148.5
May 24, 2016 (DE) .................... 10 2016 109 524.9
Jul. 6, 2016 (DE) .................... 20 2016 103 605.4

(51) Int. Cl.
*A61B 5/0205* (2006.01)
*A47C 31/00* (2006.01)
(Continued)

(52) U.S. Cl.
CPC .......... *A61B 5/6892* (2013.01); *A47C 17/162* (2013.01); *A47C 17/163* (2013.01);
(Continued)

(58) Field of Classification Search
CPC ...... A61G 7/015; A61G 7/018; A61G 7/0524; A61G 7/1065; A61G 7/1063; A61G 7/16;
(Continued)

(56) References Cited

U.S. PATENT DOCUMENTS 7,699,784 B2 * 4/2010 Wan Fong ......... A61B 5/02444
600/481
8,281,433 B2 * 10/2012 Riley .................. A61G 7/0514
5/600

(Continued)

FOREIGN PATENT DOCUMENTS

CN    1741782 A    3/2006
CN    1809315 A    7/2006
(Continued)

OTHER PUBLICATIONS

International Search Report issued by the European Patent Office in International Application PCT/EP2016/082911 dated Mar. 21, 2017.
(Continued)

*Primary Examiner* — Robert G Santos
(74) *Attorney, Agent, or Firm* — Henry M. Feiereisen LLC

(57) ABSTRACT

The invention relates to an electric motor furniture drive for sleeping or reclining furniture, comprising a number of adjusting motors (7, 8) for moving at least one movable furniture component relative to an additional furniture component by means of an electric motor and comprising a manual operation unit (10) for operating the adjusting motors (7, 8). The electric motor furniture drive is characterized in that at least one sensor (12) is provided for
(Continued)

detecting vibrations and/or sound, said sensor being coupleable to the sleeping furniture, and an analyzing unit is provided which is connected to the at least one sensor (12). The analyzing unit is designed to process and analyze the signals of the at least one sensor (12) and detect physiological parameters of a person using the sleeping or reclining furniture.

16 Claims, 10 Drawing Sheets

(51) Int. Cl.

| | | |
|---|---|---|
| A61G 7/05 | (2006.01) | |
| A61G 7/015 | (2006.01) | |
| A61G 7/018 | (2006.01) | |
| A61G 13/02 | (2006.01) | |
| A61G 13/08 | (2006.01) | |
| A61B 5/00 | (2006.01) | |
| A47C 21/00 | (2006.01) | |
| A61B 5/113 | (2006.01) | |
| A47C 27/00 | (2006.01) | |
| A61G 7/075 | (2006.01) | |
| A61G 7/10 | (2006.01) | |
| A61G 7/16 | (2006.01) | |
| A47C 20/04 | (2006.01) | |
| A47C 17/16 | (2006.01) | |
| A47C 19/02 | (2006.01) | |
| A61B 5/11 | (2006.01) | |
| G05B 19/416 | (2006.01) | |
| A61B 5/024 | (2006.01) | |
| A61B 5/08 | (2006.01) | |

(52) U.S. Cl.
CPC .......... *A47C 19/027* (2013.01); *A47C 20/041* (2013.01); *A47C 21/003* (2013.01); *A47C 27/00* (2013.01); *A47C 31/00* (2013.01); *A47C 31/008* (2013.01); *A61B 5/002* (2013.01); *A61B 5/0022* (2013.01); *A61B 5/0205* (2013.01); *A61B 5/113* (2013.01); *A61B 5/1116* (2013.01); *A61B 5/1123* (2013.01); *A61B 5/1135* (2013.01); *A61B 5/4806* (2013.01); *A61B 5/4809* (2013.01); *A61B 5/6891* (2013.01); *A61B 5/725* (2013.01); *A61B 5/746* (2013.01); *A61G 7/015* (2013.01); *A61G 7/018* (2013.01); *A61G 7/0506* (2013.01); *A61G 7/0524* (2016.11); *A61G 7/0755* (2013.01); *A61G 7/1065* (2013.01); *A61G 7/16* (2013.01); *A61G 13/02* (2013.01); *A61G 13/08* (2013.01); *G05B 19/416* (2013.01); *A61B 5/024* (2013.01); *A61B 5/02444* (2013.01); *A61B 5/0816* (2013.01); *A61G 2200/327* (2013.01); *A61G 2200/34* (2013.01); *G05B 2219/43196* (2013.01)

(58) Field of Classification Search
CPC ...... A61G 13/02; A61G 13/08; A47C 17/162; A47C 17/163; A47C 20/041; A47C 20/04; A47C 20/08; A47C 21/003; A47C 31/008; A61B 5/6892; A61B 5/6891; A61B 5/002; A61B 5/0022; A61B 5/0205; A61B 5/1116; A61B 5/1123; A61B 5/113; A61B 5/1135; A61B 5/4806; A61B 5/4809; A61B 5/725; A61B 5/746; G05B 19/416
USPC .............................. 5/616, 613, 600
See application file for complete search history.

(56) References Cited

U.S. PATENT DOCUMENTS

| | | | | |
|---|---|---|---|---|
| 8,844,073 B2* | 9/2014 | Riley | ............... | A61B 5/6891 |
| | | | | 5/424 |
| 9,320,444 B2* | 4/2016 | Hayes | .................. | A61G 7/05 |
| 9,591,995 B2* | 3/2017 | Blumberg | ............. | A47C 17/62 |
| 9,836,034 B2* | 12/2017 | Hille | .................... | G05B 15/02 |
| 10,357,413 B2* | 7/2019 | Buerstner | ............ | A61G 13/08 |
| 10,448,749 B2* | 10/2019 | Palashewski | ......... | G05B 15/02 |
| 10,729,357 B2* | 8/2020 | Larson | ................ | A61B 5/6801 |
| 2008/0005838 A1* | 1/2008 | Wan Fong | ........... | A61B 5/4094 |
| | | | | 5/600 |
| 2008/0052837 A1* | 3/2008 | Blumberg | ............. | A47C 17/04 |
| | | | | 5/727 |
| 2010/0101022 A1 | 4/2010 | Riley et al. | | |
| 2011/0263950 A1* | 10/2011 | Larson | ................... | A61B 5/026 |
| | | | | 600/301 |
| 2011/0301440 A1* | 12/2011 | Riley | ..................... | G06F 19/00 |
| | | | | 600/301 |
| 2014/0266733 A1 | 9/2014 | Hayes et al. | | |
| 2015/0019020 A1* | 1/2015 | Hille | ....................... | G05B 15/02 |
| | | | | 700/275 |
| 2015/0025688 A1 | 1/2015 | Hille et al. | | |
| 2015/0026890 A1 | 1/2015 | Hille et al. | | |
| 2015/0035457 A1 | 2/2015 | Hille et al. | | |
| 2015/0128354 A1* | 5/2015 | Greenstein | ............. | A61G 5/128 |
| | | | | 5/710 |
| 2015/0241857 A1 | 8/2015 | Hille | | |
| 2016/0081866 A1 | 3/2016 | Hille | | |
| 2016/0089287 A1* | 3/2016 | Buerstner | ............ | A61G 13/105 |
| | | | | 5/616 |
| 2016/0100696 A1* | 4/2016 | Palashewski | ........ | A61B 5/6892 |
| | | | | 700/90 |
| 2016/0377273 A1 | 12/2016 | Hille | | |
| 2019/0008283 A1* | 1/2019 | Gehrke | ................ | A47C 17/163 |
| 2019/0008284 A1* | 1/2019 | Gehrke | ................ | A61B 5/0205 |
| 2019/0021675 A1* | 1/2019 | Gehrke | ................ | A47C 21/003 |
| 2019/0357696 A1* | 11/2019 | Palashewski | .......... | G05B 15/02 |
| 2020/0383854 A1* | 12/2020 | Gehrke | ................ | A47C 31/00 |

FOREIGN PATENT DOCUMENTS

| | | | | |
|---|---|---|---|---|
| CN | 1980602 A | 6/2007 | | |
| CN | 104271005 A | 6/2007 | | |
| DE | 202016103605 U1 * | 5/2017 | ........... | A47C 17/162 |
| JP | 2005177471 A | 7/2005 | | |
| JP | 2005253957 A | 9/2005 | | |
| WO | WO 2013173640 A1 | 11/2013 | | |

OTHER PUBLICATIONS

Chinese Search Report dated Apr. 22, 2020 with respect to counterpart Chinese patent application 201680076437.0.
Translation of Chinese Search Report dated Apr. 22, 2020 with respect to counterpart Chinese patent application 201680076437.0.
Armin Hille et al., U.S. Pat. No. 9,792,810, Oct. 17, 2017, 2016-0275785-A1, Sep. 22, 2016.
Armin Hille, U.S. Pat. No. 9,478,122, Oct. 25, 2016, 2015-0130595-A1, May 14, 2015.
Armin Hille et al., U.S. Pat. No. 9,836,034, Dec. 5, 2017, 2015-0019020-A1, Jan. 15, 2015.
Armin Hille, U.S. Pat. No. 9,713,387, Jul. 25, 2017, 2015-0048763-A1, Feb. 19, 2015.
Armin Hille, U.S. Pat. No. 9,715,822, Jul. 25, 2017, 2015-0123772-A1, May 7, 2015.
Armin Hille, U.S. Pat. No. 9,252,692, Feb. 2, 2016, 2014-0159618-A1, Jun. 12, 2014.
Armin Hille, U.S. Pat. No. 9,331,610, May 3, 2016, 2014-0152068, Jun. 5, 2014.
Armin Hille, U.S. Pat. No. 9,230,764, Jan. 5, 2016, 2012-0194106, Aug. 2, 2012.

* cited by examiner

SLEEPING OR RECLINING FURNITURE AND ELECTRIC MOTOR FURNITURE DRIVE FOR SUCH FURNITURE

CROSS-REFERENCES TO RELATED APPLICATIONS

This application is the U.S. National Stage of International Application No. PCT/EP2016/082911, filed Dec. 30, 2016, which designated the United States and has been published as International Publication No. WO 2017/114945 and which claims the priorities of German Patent Applications, Serial No. 10 2015 107 148.5, filed Dec. 30, 2015, 10 2016 109 524.9, filed May 24, 2016, and 20 2016 103 605.4, filed Jul. 6, 2016, pursuant to 35 U.S.C. 119(a)-(d).

BACKGROUND OF THE INVENTION

The invention relates to an electric motor furniture drive for sleeping or reclining furniture, comprising a number of adjusting drives for moving at least one movable furniture component relative to an additional furniture component by means of an electric motor and comprising a manual operation unit for operating the adjusting motors. The invention furthermore relates to sleeping or reclining furniture, in particular a bed, comprising such an electric motor furniture drive.

Electric motor furniture drives in sleeping or reclining furniture, for example, beds, sleeper sofas, or recliners, enable a suitable sleeping or reclining position to be set in a simple manner. In beds, for example, a back or leg part can be raised or lowered in relation to a middle part of the bed. Beds equipped with electric motor drives motivate looking for and setting a best-possible sleeping position, while in contrast this is not performed in the case of beds which are nonadjustable or only manually adjustable, for reasons of convenience or because of a lack of physical movement capability.

In the clinical field, monitoring devices are known, which monitor the respiration and/or cardiac activity of a patient in sleep, to be able to engage in the event of worrying cardiac function and circulatory parameters.

In the meantime, devices for monitoring the sleep state on the basis of physiological parameters have also become commercially available for nonclinical purposes. These devices, which are placed on a night table, for example, detect noises and/or movement states during sleep by means of microphones and/or cameras. A sleep state is derived from the detected items of information and the time curve thereof is recorded. The recorded sleep curve can subsequently be retrieved and analyzed. It can be informative about how deep and restful the sleep has been.

In addition to systems which use camera and/or microphone, a sensor-based system is known, in which a pressure-sensitive sensor strip is laid over the mattress and in which the sensor strip is connected to a mobile telephone (smart phone), which records the sensor data. A heart rate and a respiratory rate, inter alia, are derived from the sensor data.

The mentioned nonclinical systems have the disadvantage that the reliability of the recognition is strongly dependent on the correct position of the monitoring devices on a night table and/or on or at the mattress. The reliability and also the usage comfort of these devices are thus restricted.

It is an object of the present invention to provide sleeping or reclining furniture and an electric motor furniture drive of the type mentioned at the outset, which further assist the user in finding deep and restful sleep.

SUMMARY OF THE INVENTION

This object is achieved by an electric motor furniture drive or sleeping or reclining furniture comprising such an electric motor furniture drive having the respective features of the independent claims. Advantageous embodiments and refinements are specified in the dependent claims.

An electric motor furniture drive according to the invention of the type mentioned at the outset is distinguished in that at least one sensor is provided for detecting vibrations and/or sounds, the sensor being able to be coupled to the sleeping furniture, and an analyzing unit is provided which is connected to the at least one sensor, wherein the analyzing unit is designed to process and analyze the signals of the at least one sensor and detect physiological parameters of a person using the sleeping or reclining furniture.

The sensor, which can be mechanically coupled to the furniture and is electrically incorporated into the system of the electric motor drive, results in a user-friendly and failsafe system with respect to incorrect operation, in particular incorrect positioning, for detecting the physiological parameters. Detected physiological parameters are preferably a heart rate, a respiratory rate, and/or a movement state of the person using the sleeping or reclining furniture.

In one advantageous embodiment, the electric motor furniture drive has a control unit for controlling the adjusting motors, wherein the analyzing unit is coupled to the control unit or is integrated into the control unit. In this manner, components of the control unit which are already provided in the electric motor furniture drive can also be used for the analyzing unit, for example, a power supply unit, communication devices, and/or a housing including the connection options. Moreover, wiring of the sensor on or below the bed is simplified if the existing structure of the electric motor furniture drive is used.

In a further advantageous embodiment of the electric motor furniture drive, the at least one sensor has a piezo-electrically or electromagnetically operating sound and/or vibration pickup. Such a sensor works robustly and is capable of recording both vibrations (structure-borne sound) and also airborne sound, wherein it can be established by the design in which ratio these different types of sound are detected. Furthermore, multiple sound and/or vibration pickups can also be combined, wherein, for example, a piezo-electrically and electromagnetically operating sound and/or vibration pickup are arranged at the same position or at different positions. The sensor preferably has a sensor housing having an installation surface, on which a protrusion is formed, wherein a sound and/or vibration pickup of the sensor is arranged in the interior of the sensor housing in the region of the protrusion. In this manner, a particularly good vibration transmission from the furniture component on which the sensor is installed to the sound and/or vibration pickup can be achieved. The installation surface, which can be, for example, part of an installation plate having fastening holes, can be fastened in an uncomplicated manner on a planar bed component. Such a planar bed component is, for example, a plate-shaped back part of a support element of a bed. An installation adapter is preferably provided for installation on a slatted frame as a support element, which is connected to the sensor housing in order to enclose a slat of the slatted frame to install the sensor on this slat.

The analyzing unit preferably has a filter, in particular a low-pass or bandpass filter for signal processing. Alternatively or additionally, a first signal processing can already also take place in the sensor housing, for example, by arranging a signal amplifier and/or an analog and/or digitally operating signal filter in the sensor housing. A transmission of the measurement signal to the analyzing unit which is less susceptible to interference is thus achieved.

Furthermore, the analyzing unit can have a storage unit for storing a time curve of the physiological parameters. The analyzing unit can moreover have a monitoring device for comparing the physiological parameters to predefined limiting values, in order that, in a case in which a health risk is recognized for the person, this person or a further person can be warned. For this purpose, the analyzing unit preferably has a transmission unit for transmitting the physiological parameters to a mobile device or is coupled to a transmission unit provided in the control unit of the electric motor furniture drive. The transmission unit is preferably designed for wireless transmission of the physiological parameters to the mobile device, in particular via a WLAN or Bluetooth transmission link. If the physiological parameters are transmitted to the mobile device, a comparison of the physiological parameters to predefined limiting values can also be performed in the mobile device. In addition, the mobile device can represent the manual operation unit for the furniture drive, which saves material and costs for a separate manual operation unit and permits more comfortable operation, since multiple separate devices do not have to be positioned ready to hand in the region of the furniture.

In a further advantageous embodiment of the electric motor furniture drive, the analyzing unit for the signals of the sensor is additionally designed to detect and analyze vibrations which occur upon the actuation of one or more of the adjusting drives. In this manner, as a positive secondary use, the sensor can be used to determine a malfunction and/or an overload and/or a non-load of one or more of the adjusting drives in operation. The determined states indicate technical problems, which have already occurred or are possibly imminent, of the adjusting drives, or incorrect use.

A sleeping or reclining furniture according to the invention, in particular a bed, is distinguished in that an above-described sensor is fastened on the sleeping or reclining furniture, preferably on a furniture part of the sleeping or reclining furniture. The sensor is particularly preferably fastened on a back part of the sleeping or resting furniture, since in this manner vibrations from the chest cavity of a person using the sleeping or resting furniture can be detected particularly well, which permit inferences about the respiration and circulation of the person. Positioning of the sensor in a lower half and in particular in a lower third of the back part of the sleeping or resting furniture is particularly well suitable in this respect. To utilize vibration modes and possibly resonances of the back part, it is advantageous to arrange the sensor in a region of an anti-node of a natural vibration mode of the back part. The back part, or more generally the furniture part on which the sensor is fastened, then becomes part of the system for recording the vibrations or oscillations and is used as a sound conductor and to some extent as an "antenna" for the vibrations. It is advantageous in this case to fasten the sensor between fastening points of a fitting element, which couples the back part to one of the adjusting drives, on the back part of the sleeping or reclining furniture. Such a fitting element influences the natural vibration modes of the back part due to its stability. It is designed, for example, as a tripod having three contact points spaced apart from one another on the back part. An antinode having a large vibration amplitude generally lies in the region between the contact points.

BRIEF DESCRIPTION OF THE DRAWING

The invention will be explained in greater detail hereafter on the basis of exemplary embodiments with the aid of figures. In the figures.

DETAILED DESCRIPTION OF PREFERRED EMBODIMENTS

Figure 1:
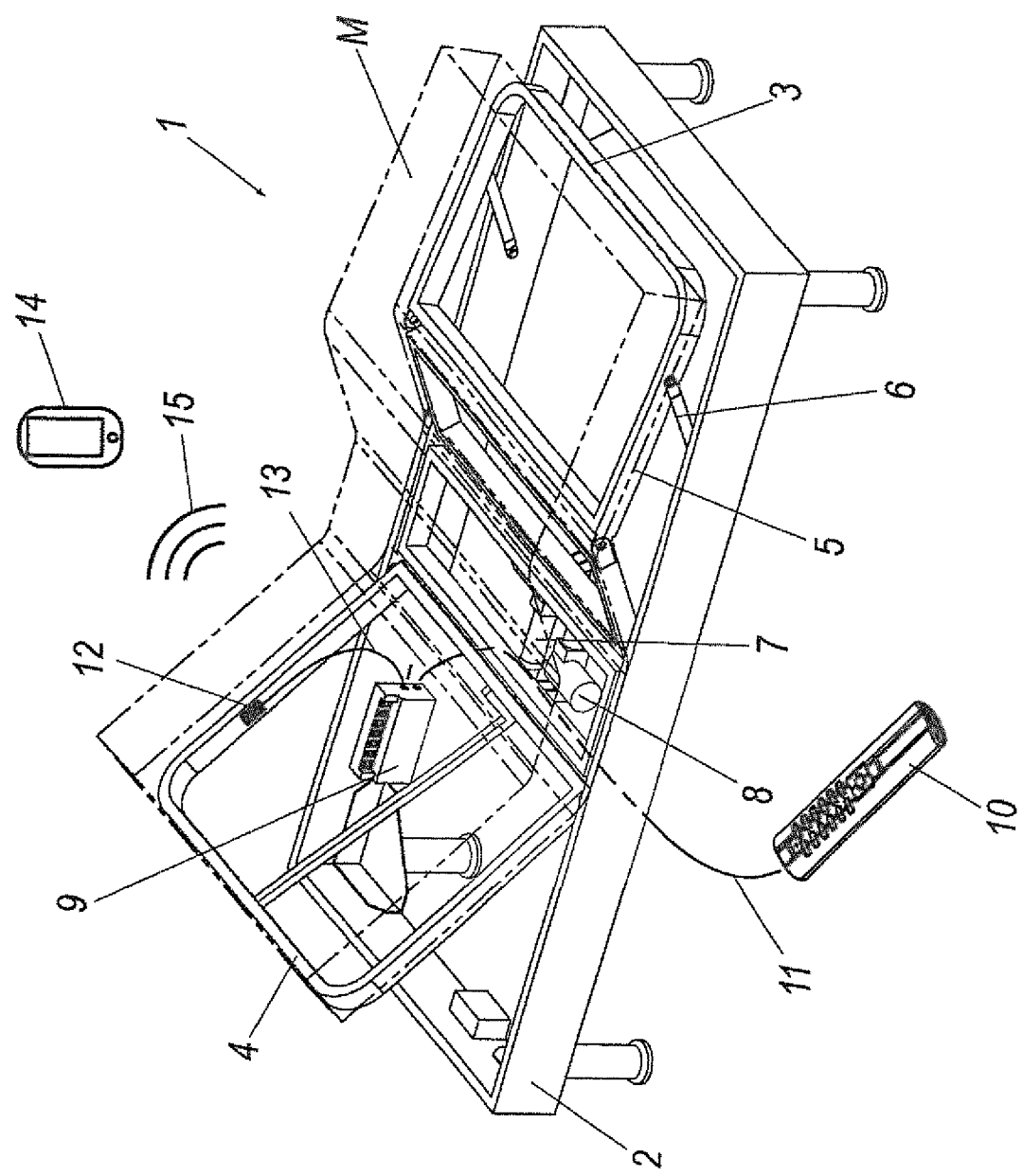
FIG. 1 shows a first exemplary embodiment of sleeping furniture comprising an electric motor furniture drive and a sensor in an isometric view.

FIG. 1 shows a bed 1 as an example of sleeping furniture comprising an electric motor furniture drive. The bed 1 has at least one support element 3 for accommodating, for example, padding or a mattress M. The bed 1 can be designed as a single bed for one person or also as a double bed for multiple persons. The support element 3 is designed, for example, as a slatted frame, as a planar support surface, or the like and is on a base element 2, a framework having feet here, using which the bed 1 is set up at a setup location, for example, a floor.

The support element 3 has, in the illustrated example, a back part 4 and a leg part 5, which are arranged so they are movably mounted relative to a fixed middle part here or relative to the base element 2. This movable arrangement is implemented here by means of a so-called movement fitting 6. The movement is designed as displaceable and/or pivotable.

The movably mounted back part 4 and the leg part 5 are each coupled to an electric motor adjusting drive 7, 8. The back part 4 is thus coupled to the electric motor adjusting drive 7. The electric motor adjusting drive 8 is provided for the movement and/or adjustment of the leg part 5.

The electric motor adjusting drives 7, 8 are designed in the present case as linear drives. The linear drives have one or a number of electric motors, wherein a speed-reducing gear having at least one gear step is connected downstream of each motor. A further gear, for example, in the form of a threaded spindle gear, which generates a linear movement of an output element from the rotational movement of the motor, can be connected downstream of the speed-reducing gear. The last gear element or a further element connected thereto forms the output element. The output element of the respective electric motor furniture drive is connected to the respective furniture component (back part 4, leg part 5) or alternatively to a component connected to the base element 2, so that in the event of an operation of the electric motor of the respective adjusting drive 7, 8, the movable furniture components 4, 5 are adjusted relative to one another and/or relative to the base element 2.

The electric motor adjusting drives 7, 8 are connected to a control unit 9. This connection can be embodied, for example, as a pluggable cable connection, which is not shown in greater detail here. The control unit 9 has an electrical supply unit, which provides the electrical energy, for example, from a power supply network, for the electric motor adjusting drives 7, 8. For this purpose, the control unit 9 is connectable via a network cable (not shown in this example) having a network plug to a network terminal. The network plug conducts the input-side network voltage via the network cable to the electrical supply unit of the control unit 9, which emits a low voltage in the form of a DC voltage on the secondary side.

Alternatively thereto, an external network-dependent power supply having network input and having secondary side low-voltage output is connected upstream of the control unit 9, which supplies the low voltage in the form of a DC voltage via the line.

In an alternative embodiment, the control unit is not arranged in a separate housing, but rather integrated in one of the adjusting drives 7, 8. This adjusting drive then represents a main drive, to which further adjusting drives can optionally be connected.

In a further alternative embodiment of an electric motor furniture drive, the control unit can be arranged distributed in the system such that each of the adjusting drives 7, 8 has a motor controller itself and has a bus communication interface, via which the adjusting drives 7, 8 are connected to one another and to further components. It can be provided in this case that at least one of the adjusting drives 7, 8 has a separate power supply unit for its power supply or for the supply of multiple or all provided adjusting drives and/or possibly further system components.

A manual operation unit 10 is provided, which has operating elements, using which the electromechanical adjusting drives 7, 8 are controllable via the control unit 9. The manual operation unit 10 can be connected via a cable to the control unit 9 in one exemplary embodiment. Alternatively, the manual operation unit 10 can be provided with a transmitting device for a wireless transmission of signals to the control unit 9. The wireless transmission can be implemented by a radio transmission link, an optical transmission link (for example, for infrared light), and/or an ultrasound transmission link, wherein the control unit 9 is equipped with a respective corresponding receiving unit. Furthermore, the manual operation unit can alternatively also form the control unit for the adjusting drives, for example, by the operating current of the adjusting drives being switched directly via switches of the manual operation unit.

The operating elements can be designed, for example, as buttons and/or switches. Furthermore, the manual operation unit 10 can be equipped with a reporting element, for example, a light-emitting diode or a display unit. The reporting element is used, for example, for function display and/or feedback, error displays, etc.

According to the application, a sensor 12, which detects vibrations and/or sound, is provided in the illustrated bed 1. The sensor 12 is fastened in the illustrated exemplary embodiment on a frame component of the back part 4. The fastening can be a screw or rivet connection or an adhesive bond or can also be a catch or clamp connection, for example, with the aid of a spring clamp which encloses the corresponding frame component. The sensor 12 is designed, for example, as a piezoelectric component or as an electromagnetic component and/or has a sound and/or vibration pickup operating in this manner and is sensitive to vibrations of the underlying surface on which it is fastened, in the present case thus for oscillations (vibrations) which the frame of the back part 4 experiences. Such vibrations also comprise structure-borne sound, which is relayed by the back part. In addition, the sensor 12 can be sensitive to (airborne) sound waves and can function in this meaning as a microphone. A further suitable sensor is an electromechanical sensor, for example, a micromechanical acceleration sensor.

The sensor 12 is connected via a sensor cable 13 to the control unit 9. If necessary, a power supply for the sensor 12 is provided and signals output by the sensor 12 are relayed to the control unit 9 via the sensor cable 13. In an alternative embodiment, the sensor 12 can be coupled via a wireless connection, for example, a radio connection, to the control unit 9. In this case, the sensor 12 is provided with a separate power supply, for example, in the form of a possibly rechargeable battery.

The control unit 9 comprises an analyzing unit for processing and analyzing the signals supplied by the sensor 12. The analyzing unit comprises, for example, amplifiers and filter units, which enable certain physical functions of a person located in the bed 1 to be inferred from the signal transmitted by the sensor 12. In particular, the analyzing unit is configured for the purpose of ascertaining physiological parameters of the person from the signals of the sensor 12. Such parameters relate, for example, to cardiac and circulatory functions and comprise, for example, a heart rate and a respiratory rate. Furthermore, it can be ascertained whether the person located in the bed is snoring. Moreover, movements of the person are detected. Details on the ascertainment of the mentioned parameters from the signals of the sensor 12 will be explained in greater detail hereafter in conjunction with FIG. 3.

The determined parameters are transmitted either immediately or after buffering in the control unit 9 as wireless signals 15 to a mobile device 14. The mobile device 14 can be in particular a commercially available mobile telephone ("smart phone") or a tablet computer and is equipped with corresponding software ("app"), which enables analysis and preferably graphic display of the time dependence of the ascertained sleep parameters. WLAN (wireless local area network) or Bluetooth, for example, can be used as the transmission link for the wireless signals 15.

Moreover, a comparison of the measured physiological parameters to predefined limiting values for these parameters can be provided in the control unit 9. If the ascertained parameters are transmitted immediately, i.e., without long buffering in the control unit 9, during the sleep phase to the mobile device 14, such a comparison can alternatively or additionally take place therein. If the parameters exceed or fall below the limiting values or one or more of the parameters leave a predefined range, it is provided that the control unit 9 or the mobile device 14 outputs an alarm signal. This alarm signal can be output optically and/or acoustically directly by the control unit 9 and/or the mobile device 14. Alternatively or additionally, it can be provided that the mobile device 14 emits an alarm message via a further wireless transmission link (not shown here) (for example, WLAN, mobile radio network). In this manner, a further person can be informed if undesired sleep parameters are shown. The illustrated bed 1 and/or the electric motor furniture drive comprising the sensor 12 can thus also be used for clinical monitoring and/or patient monitoring or for monitoring small children to protect from sudden infant death. For example, an alarm message can be emitted if a person has left the bed, possibly if a person has left the bed since a predetermined time, or if no physiological parameters or only physiological parameters considered to be critical are detected.

In the illustrated exemplary embodiment, the sensor 12 is arranged on a frame element of the back part 4. Other arrangements on the sleeping furniture, i.e., the illustrated bed 1, or elements connected thereto, such as the mattress M laid thereon, are possible. The sensor 12 can be installed, for example, on a slatted frame (not visible here), which is laid on the support element 3. Installation secure against slipping in or on the mattress M is also possible. Furthermore, the use of multiple sensors 12 which are positioned at different points in or on the bed 1 is possible.

The connection to the control unit 9, which is arranged inside the bed 1, prevents the sensor cable 13 having to be laid outside the bed 1. The fixing of the sensor 12 in or on the bed 1 ensures correct positioning of the sensor 12 at all times and thus reliable analysis of the data of the sensor 12.

Figure 2:
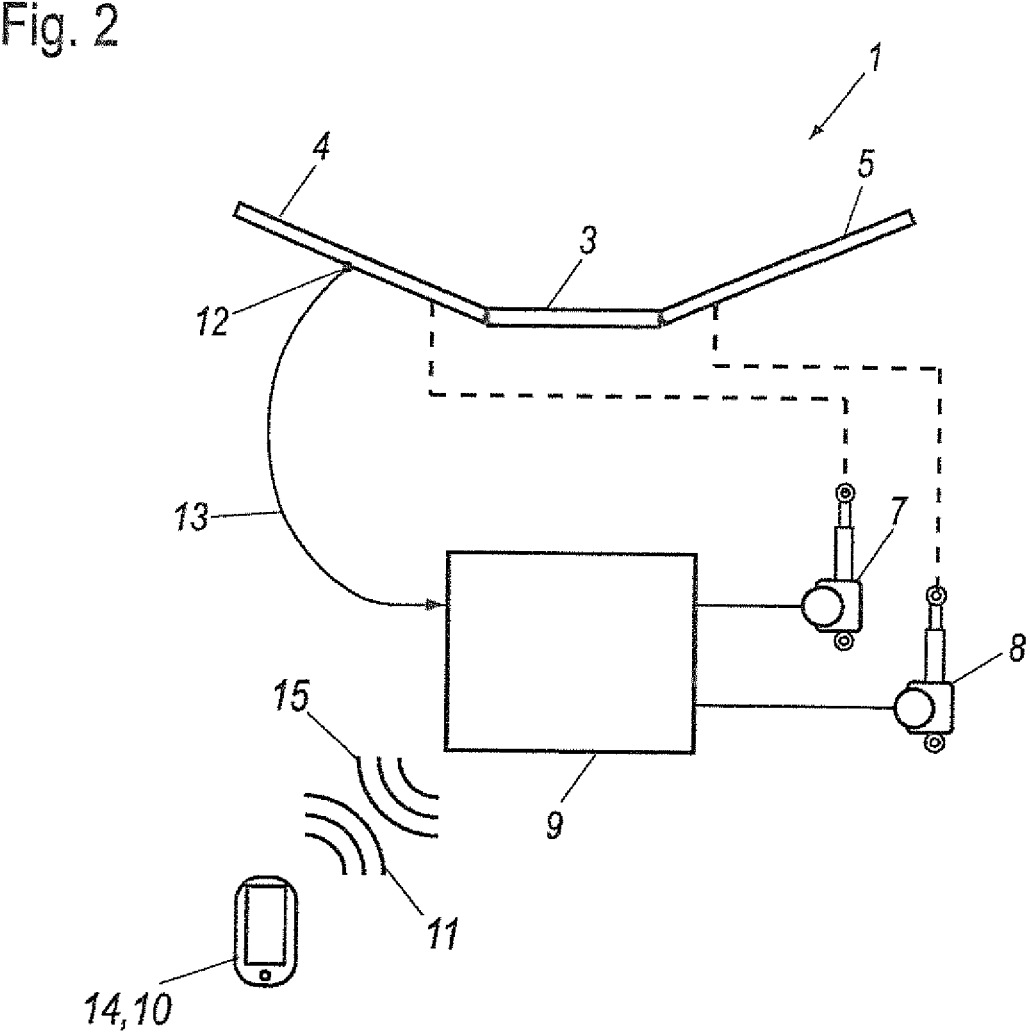
FIG. 2 shows a second exemplary embodiment of sleeping furniture comprising an electric motor furniture drive and a sensor in a schematic block diagram.

FIG. 2 shows a second exemplary embodiment of sleeping furniture comprising an electromechanical furniture drive and an integrated sensor 12 in a schematic block diagram. A bed 1 is again shown as an example of sleeping furniture. Identical reference signs identify identical or identically acting elements as in FIG. 1 in the exemplary embodiment of FIG. 2. In its basic structure, the electric motor furniture drive according to FIG. 2 corresponds to that shown in FIG. 1. Reference is hereby made to the preceding description.

In contrast to the exemplary embodiment of FIG. 1, in the present case the mobile device 14 also assumes the function of the manual operation unit 10. Corresponding software ("app") for the function as the manual operation unit 10 is again installed on the mobile device.

The transmission link between the mobile device 14 and the control unit 9 is embodied as bidirectional, so that control instructions to the adjusting drives 7, 8 can be transmitted from the mobile device 14 used as the manual operation unit to the control unit 9, and data which relate to the sleep state can be transmitted from the control unit 9 to the mobile device 14.

In the exemplary embodiments of FIGS. 1 and 2, the analyzing unit for the signals of the sensor 12 is integrated into the control unit 9. Alternatively, it is possible to form the analyzing unit separately from the control unit 9 in a separate housing. The analyzing unit can then be electrically coupled to the control unit 9 to transmit the ascertained physiological parameters. A use of such an autonomous analyzing unit detached from the control unit 9 is also possible, in particular if a transmission unit is already provided in the housing of the analyzing unit for the wireless transmission of the ascertained physiological parameters and/or preprocessed signals of the sensor 12 to the mobile device 14.

Figure 3:
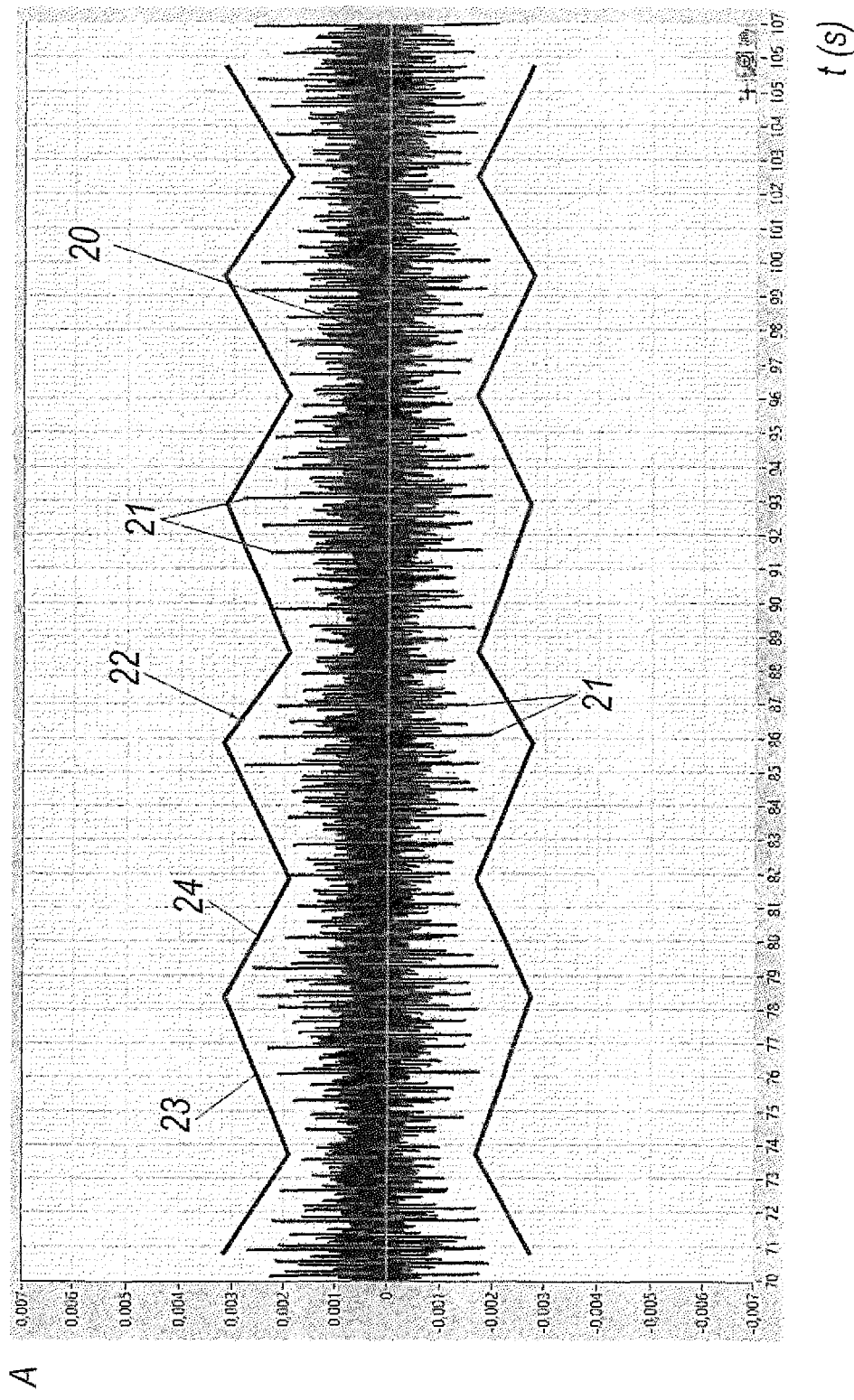
FIG. 3 shows a depiction of a time dependence of sensor data.

FIG. 3 shows a detail of a measured signal 20 of the sensor 12 in a diagram. The time curve t in seconds is indicated on the horizontal axis. A signal amplitude A in arbitrary units is shown on the vertical axis.

The portion shown of the signal curve of the signal 20 is during a calm sleep phase without movement and without snoring of the observed person. A movement of the person is expressed in amplitudes which exceed those shown by a factor of several tens to hundreds. Movements may therefore be identified very easily. A snore and the vibrations accompanying it can also be clearly differentiated from the illustrated signal curve, since they are reflected in an amplitude greater by multiple times.

In the curve of the signal 20 shown in FIG. 3, regular peaks 21 are observable, which originate from the heartbeat of the person and are referred to as heartbeat peaks 21 hereafter. A heart rate can be ascertained from the interval of the heartbeat peaks 21. The time interval of adjacent heartbeat peaks 21 permits statements about the pulse uniformity, which can be a measure of the depth of the sleep.

Furthermore, it can be seen in FIG. 3 that the amplitude of the heartbeat peaks 21 varies regularly at a lower frequency. This variation is illustrated by an envelope curve 22. The envelope curve 22 displays alternating rising flanks 23 and falling flanks 24. The curve of the envelope curve 22 is correlated with the breathing of the person. The rising flanks 23 identify an inhalation phase and the falling flank 24 identifies an exhalation phase.

The example of FIG. 3 shows how cardiovascular parameters can be concluded from the signals of the sensor 12, in the present case pulse and respiration. In a similar manner, further sleep parameters, such as movement states and snoring, can be ascertained.

Filtering of the raw signals of the sensor 12 is carried out, in particular by means of a low-pass filter, for the analysis of the signals 20. The use of a bandpass filter having suitable base frequencies is also possible. Low-pass or bandpass filters are used to eliminate interfering frequencies. The processing of the signals is preferably carried out with the aid of a digital signal processor (DSP).

The sensor 12 can additionally or alternatively also be used for monitoring the correct function of the electric motor drive. An actuation of the adjusting drives 7, 8 results in a movement of the moving furniture parts, for example, of the back part 4 and/or the leg part 5. In addition, the actuation of the adjusting drives 7, 8 results in vibrations of these furniture parts and also of the entire furniture, which are also detected by the sensor 12. These vibrations occur in a typical frequency range. The signal curve reflects the motor movement of the adjusting drives 7, 8. A first typical relevant frequency range is in the range of the motor speed of the motors of the adjusting drives 7, 8. Faults on the motor itself or an output gear wheel are shown in this frequency range. A further typical relevant frequency range corresponds to an integer fraction according to a transmission ratio of the gear, which is approximately 1:30 to 1:50. Faults in downstream gear stages or roller bearings are indicated in this frequency range. A third typical frequency range is in the range of squeaking noises of hinges, which are part of a furniture fitting. Shape and amplitude are, on the one hand, typical for the adjusting drive 7, 8 used, on the other hand, they give information about the correct function of the adjusting drives 7, 8 and the wear state thereof.

An overload of one of the adjusting drives 7, 8 can also be recognized on the basis of the signal form of the signals of the sensor 12. The sensor 12 can thus function, for example, as a pinch protection, wherein the control unit 9, in the event of overload of one of the adjusting drives 7, 8, stops this drive and/or causes it to run in the opposite direction. An underload on the adjusting drive 7, 8 can also be an indication of pinching, for example, if a furniture part (back part 4, leg part 5) is released and the adjusting drive 7, 8 is operated nearly without force, this indicates pinching of a body part under the moving furniture part which is sinking down. An adjusting drive 7, 8 operated without load is also identifiable on the basis of the signals of the sensor 12.

Two further exemplary embodiments of a bed 1 as an example of sleeping furniture comprising an electric motor furniture drive comprising adjusting drives 7, 8 and a control unit 9 and also a sensor 12 for detecting vibrations and/or sound are illustrated in FIGS. 4 to 7 hereafter. In all exemplary embodiments, identical reference signs identify identical or identically acting elements as in the above-described examples.

For reasons of comprehensibility, a manual operation unit 10 having transmission link 11 and a mobile device 14 and the wireless signals 15 exchanged using them, as shown in FIGS. 1 and 2, are not shown in FIGS. 4 to 7. It is apparent that the control unit 9 can be coupled in these exemplary embodiments in the same or a comparable manner to the mentioned manual operation units 10 and/or mobile devices 14 as shown in FIGS. 1 and 2 and described in conjunction with these figures.

Figure 4:
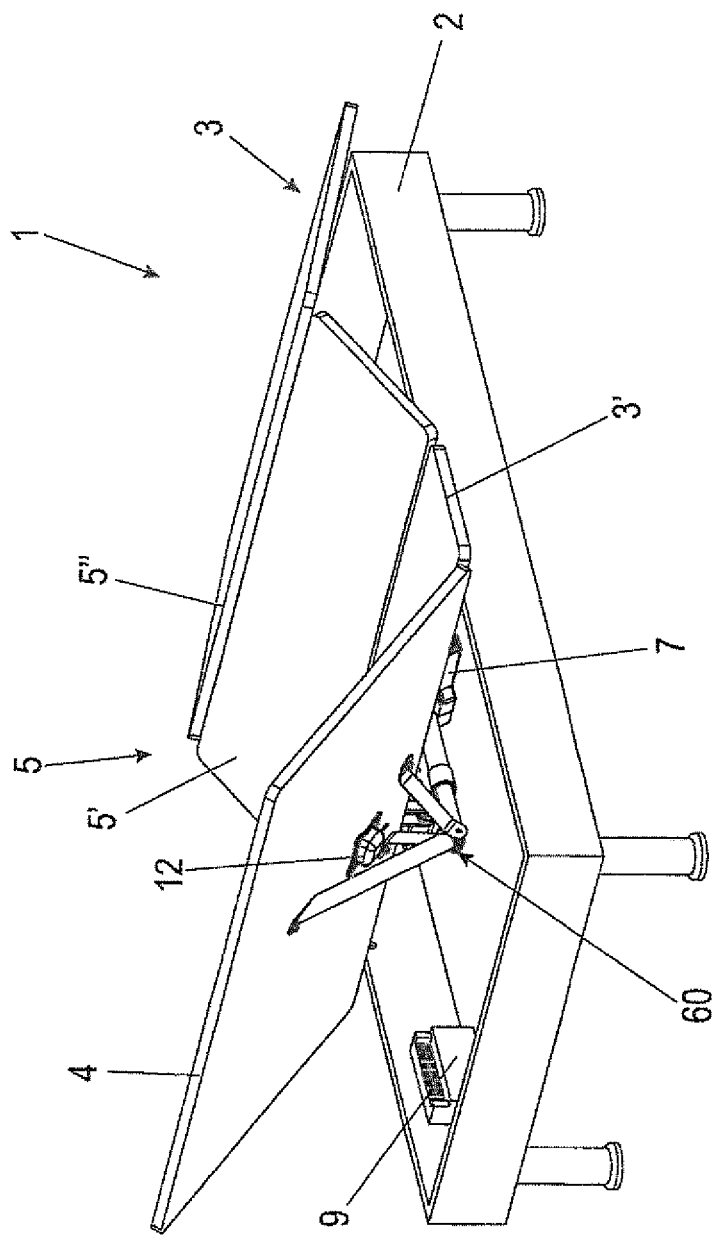
FIG. 4 shows a third exemplary embodiment of sleeping furniture comprising an electric motor drive and a sensor in an isometric view.
Figure 5:
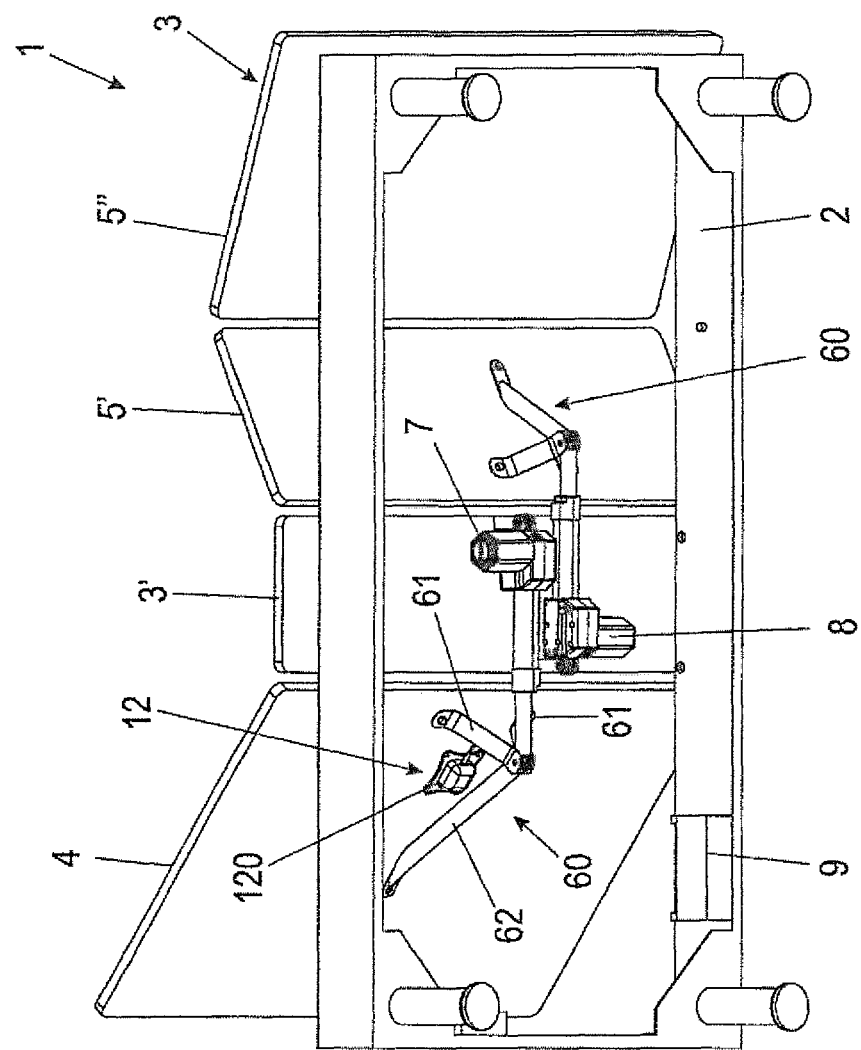
FIG. 5 shows the sleeping furniture according to FIG. 4 in an isometric view diagonally from below.

The third exemplary embodiment of the bed 1 is illustrated in each of FIGS. 4 and 5 in an isometric view from two different viewing directions. The bed 1 again has a framework with feet, which represents a base element 2. It is apparent that instead of the frame-type framework having the separately formed feet, a rather box-shaped framework having four side walls which extend to the floor can also be formed.

The base element 2 bears a support element 3, which accommodates padding, in particular a mattress (not shown here). Although the illustrated bed 1 is a single bed for one person, it can be designed in the same manner as a double bed for multiple persons.

In the present case, the support element 3 does not have a supporting frame, which accommodates, for example, a slatted frame as an underlying surface of the padding or the mattress, but rather essentially self-supporting plates. Such a bed concept is implemented, for example, in so-called box spring beds, in which the mattress is thicker than conventional mattresses and contains spring elements, which offer sufficient sleep comfort without a springy underlying surface, for example, like that represented by a slatted frame.

The support element 3 in turn has multiple sections adjustable in relation to one another, specifically a middle, non-pivotable section 3', a back part 4 pivotable relative thereto, and a two-part leg part 5. A first section 5' of the leg part 5 is coupled in this case so it is pivotable in relation to the support element 3. A second section 5" of the leg part 5 is articulated with a free transverse side of the first section 5' and is accordingly also raised at the connecting line of the two sections 5' 5". Pivot fittings, for example, in the form of hinge brackets, are arranged along the connecting lines between the non-pivotable section 3' of the support element 3 and the back part 4 or the first section 5' of the leg part 5, and on the connecting line between the first and the second sections 5', 5" of the leg part 5. The non-pivotable section 3' is fixed in relation to the base element 2 in the present case.

FIG. 5 shows the bed 1 of the third exemplary embodiment in a view diagonally from below. In this view, the electric motor furniture drive and its coupling to the various parts of the support element 3 can be recognized well. As in the first and second exemplary embodiments, two adjusting drives 7, 8 are provided, which are both coupled at one of the sides thereof to the non-pivotable section 3' of the support element 3. At a movable output side, which is linearly extendable here, the two adjusting drives 7, 8 are each coupled to a fitting element 60, which is installed on the back part 4 or the first leg part 5', respectively. The fitting element has the form of a tripod here in each case, wherein two transverse supports 61 laterally define the force introduction point of the respective adjusting drive 7, 8 and a longitudinal support 62 introduces the adjusting force into the back part 4 or the leg part 5, respectively.

As is apparent in FIGS. 4 and 5, the sensor 12 is installed using a sensor housing 120 on the lower side of the back part 4. The installation position is advantageously approximately in the middle in the transverse direction of the bed 1 and approximately in the region of the lower third of the back part 4, which is adjacent to the non-pivotable section 3' of the support element 3, with respect to the longitudinal position within the bed 1.

The sensor 12 is particularly advantageously installed within a triangle, the corner points of which are defined by the fastening points of the fitting element 60 on the back part 4. In the illustrated position, the sensor 12 is located in a physiologically reasonable position, since the sensor 12 is approximately at the height of the thorax, from which in sleep the heartbeat movement and also respiration movements and respiration noises are transmitted via the mattress to the back part 4 of the bed 1. Furthermore, natural vibrations of the back part 4 are relevant for a signal detection by the sensor 12. These natural vibrations are determined by the shape and size of the back part 4 itself and also by the fastening points of the fitting element 60, which is coupled to the adjusting drive 7.

In the event of a vibration excitation of the back part 4, the connecting points to the fitting element 60 represent regions having lower vibration amplitude. However, an at least local maximum of the vibration amplitude for a vibration mode of the back part 4 is provided in a section between these points.

The housing 120 of the sensor 12 illustrated in FIGS. 4 and 5 will be explained in greater detail in conjunction with FIGS. 8 and 9.

Figure 6:
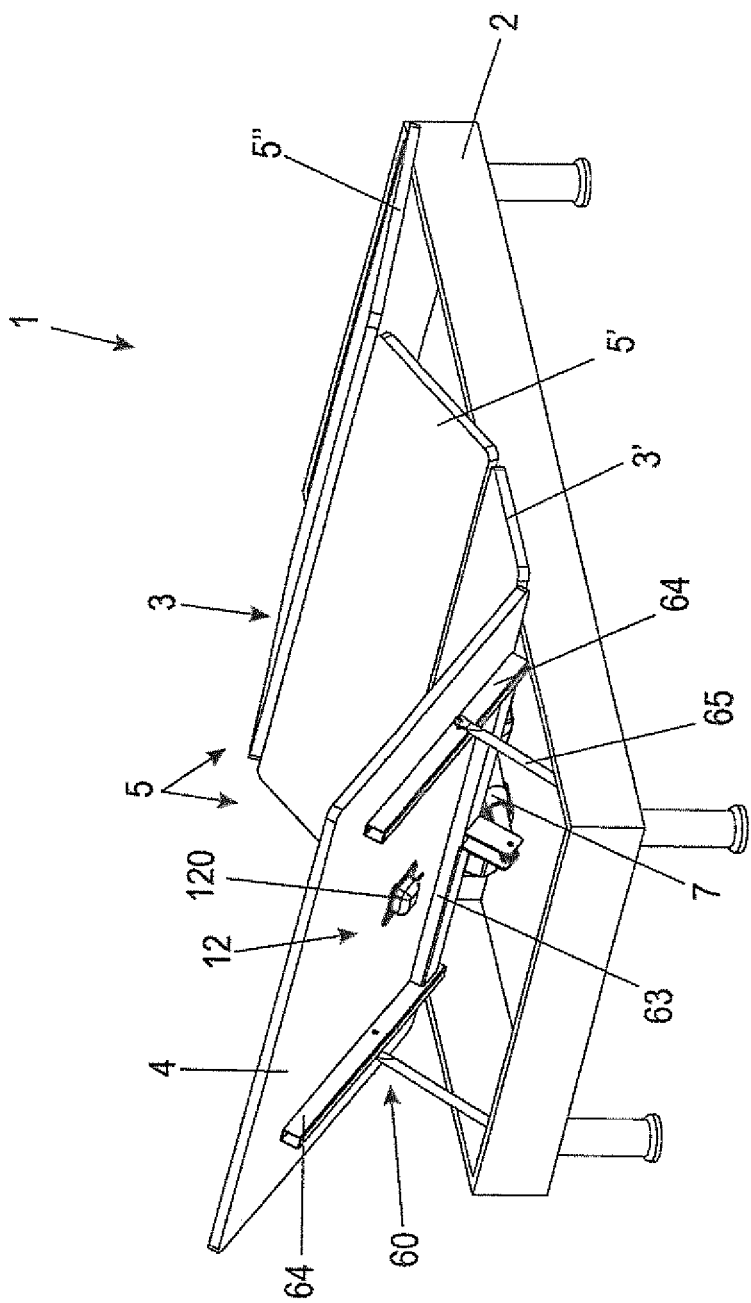
FIG. 6 shows a fourth exemplary embodiment of sleeping furniture comprising an electric motor drive and a sensor in an isometric view.
Figure 7:
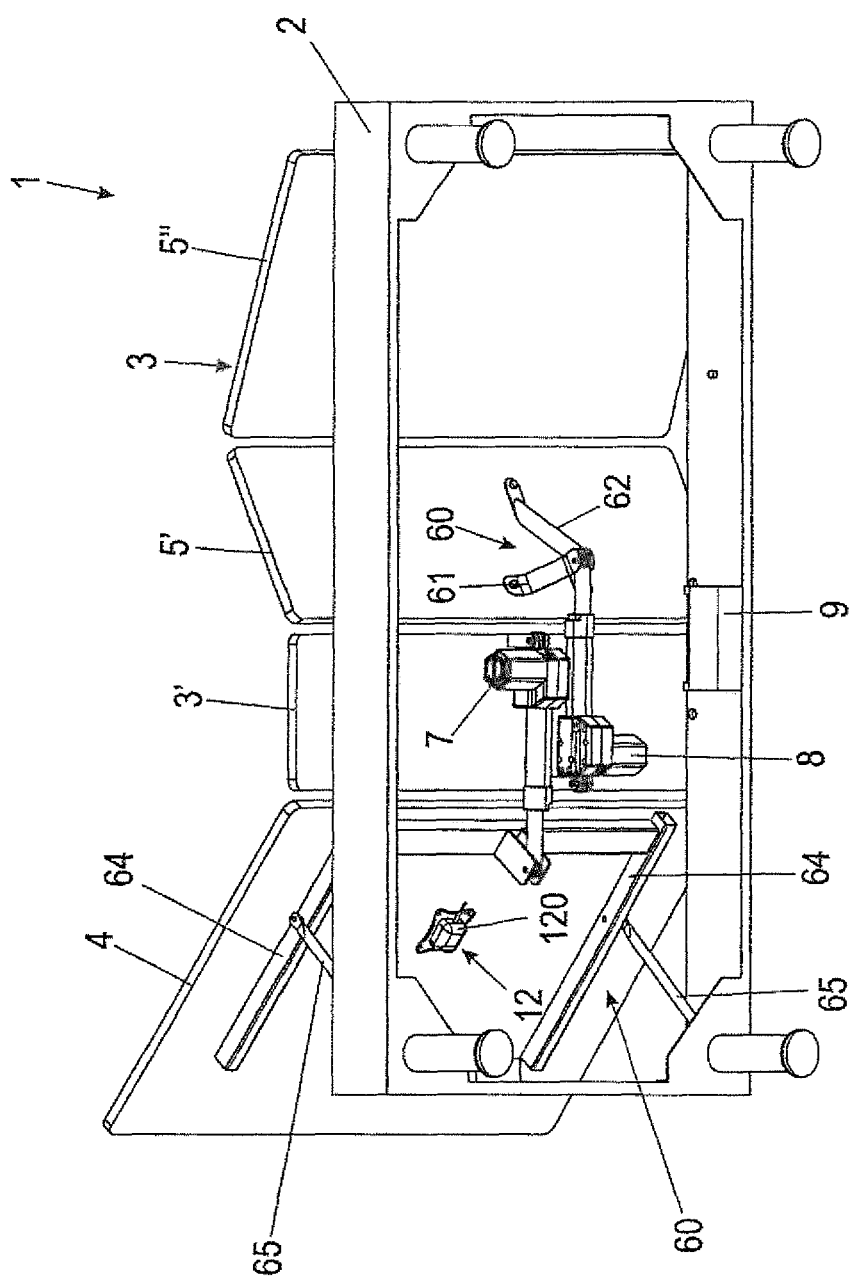
FIG. 7 shows the sleeping furniture according to FIG. 6 in an isometric view diagonally from below.

A further exemplary embodiment of a bed 1 comprising an electric motor drive and sensor 12 for recording vibration and/or sound is illustrated in FIGS. 6 and 7. FIG. 6 shows an isometric view diagonally from above and FIG. 7 shows a view with viewing direction of the lower side of the bed 1.

As in the exemplary embodiment of FIGS. 4 and 5, the bed 1 also has a support element 3 comprising plate-shaped sections here a non-pivotable section 3', a back part 4 pivotable relative thereto, and a leg part 5, of which a first section 5' is pivotable by means of an electric motor relative to the non-pivotable section 3'.

In this exemplary embodiment, the type of the force transmission and the movement kinematics of the back part 4 are different from the exemplary embodiment of FIGS. 4 and 5. A U-shaped frame is screwed onto the back part 4 as a fitting element 60 for force transmission, the base 63 of which extends in the transverse direction of the bed 1 in the region of the connection of leg part 4 and non-pivotable section 3'. Two legs 64 originating from this base 63 extend in the longitudinal direction of the bed 1, in each case in the side region of the back part 4. They are linked by levers 65 on the base element 2 of the bed 1. In this embodiment of the bed 1, the non-pivotable section 3' is mounted so it is displaceable in the longitudinal direction on the base element 2. Upon pivoting up of the back part 4, it is essentially maintains its longitudinal position and the non-pivotable section 3' and the leg part 5 follow the movement of the lower connecting line between the back part 4 and the non-pivotable section 3'.

The sensor element 12 is also arranged in this case in the middle in the transverse direction of the bed 1 and in the lower third of the back part 4 in the longitudinal direction of the bed 1. As in the exemplary embodiment of FIGS. 4 and 5, the sensor is installed in a region of the back part 4 which lies inside the assistance points by the furniture fitting, using which the back part 4 is coupled to the adjusting drive 7.

Figure 8:
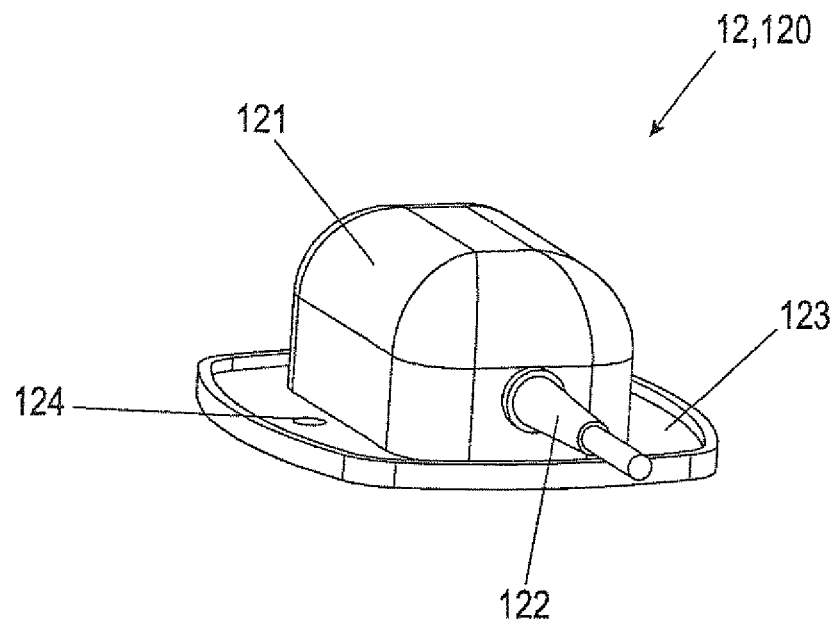
FIGS. 8 and 9 each show an isometric illustration of a sensor having sensor housing from various viewing directions.
Figure 9:
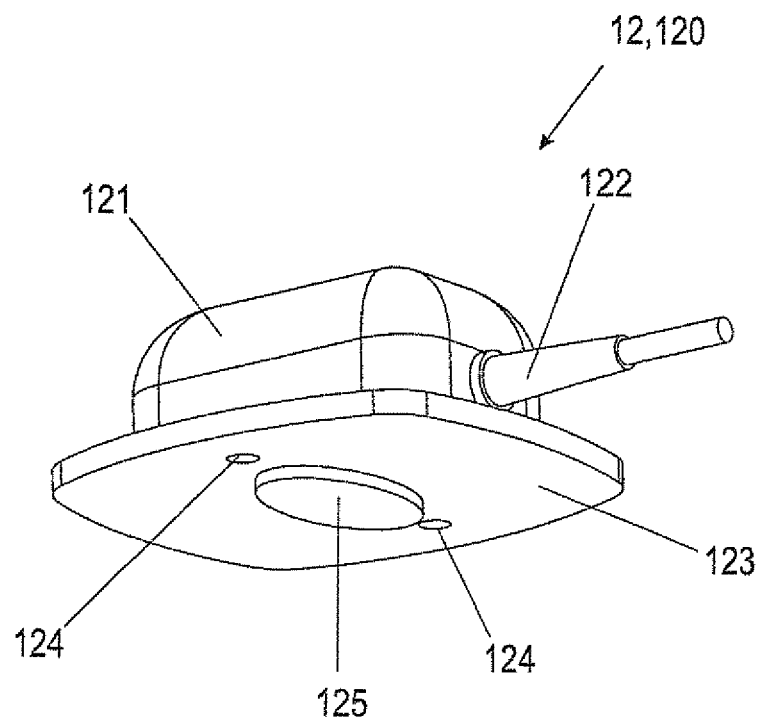

An isometric illustration of the sensor 12 comprising the sensor housing 120 is illustrated in each of FIGS. 8 and 9, which is already illustrated in conjunction with FIGS. 4 to 7. The sensor housing 120 is illustrated in FIG. 8 in a diagonal view of its upper side and in FIG. 9 in a diagonal view with view of its lower side.

The sensor 12 is used to record vibrations, in particular structure-borne sound vibrations, which are transmitted from the component of the bed on which it is installed to the sensor 12. As already mentioned in conjunction with FIGS. 1 and 2, the sensor 12 can use various physical basic principles for converting sound into an electrical signal, for example, an electromagnetic principle, in which a coil and a permanent magnet move in relation to one another. A capacitive principle is also possible. Furthermore, the sensor 12 can make use of piezoelectric effects, by arranging piezoelectric active material between two plate-shaped metallic electrodes. Such a sensor is sensitive in particular to a bending vibration. A further suitable sensor is an electromechanical sensor, for example, a micromechanical acceleration sensor.

The illustrated sensor housing 120 has a cupola-shaped housing part 121, in which the actual sound and/or vibration pickup is arranged. A cable feedthrough 122, preferably having buckling protection, is used for feeding through the sensor cable 13. The cupola-shaped housing part 121 is arranged in the middle on an installation plate 123. It has fastening holes 124, for example, for a screw installation.

As is apparent in FIG. 9, a protrusion 125, using which the sensor 12 presses against a planar surface upon installation on this surface, is arranged on the lower side of the installation plate 123, which faces toward the furniture part, for example, the back part 4. A vibration transmission therefore takes place in particular in the region of the protrusion 125. In the interior of the housing 120, the actual sound and/or vibration pickup is arranged with its vibration-sensitive region preferably above the protrusion 125. In addition, the protrusion 125 can optionally be continued inward, so that a direct transmission to the vibration-sensitive section of the sound and/or vibration pickup takes place. In this manner, structure-borne sound is transmitted as directly as possible to the sound and/or vibration pickup.

In addition, sufficient structural space for analyzing electronics is provided in the cupola-shaped housing part 121, so that signal processing of the sensor signal can take place directly in the sensor housing 120. This signal processing can include amplification and/or filtering of the signal emitted by the sound and/or vibration pickup. Corresponding power supply lines for the analyzing electronics in the sensor housing 120 can be provided in the sensor cable 13.

Figure 10:
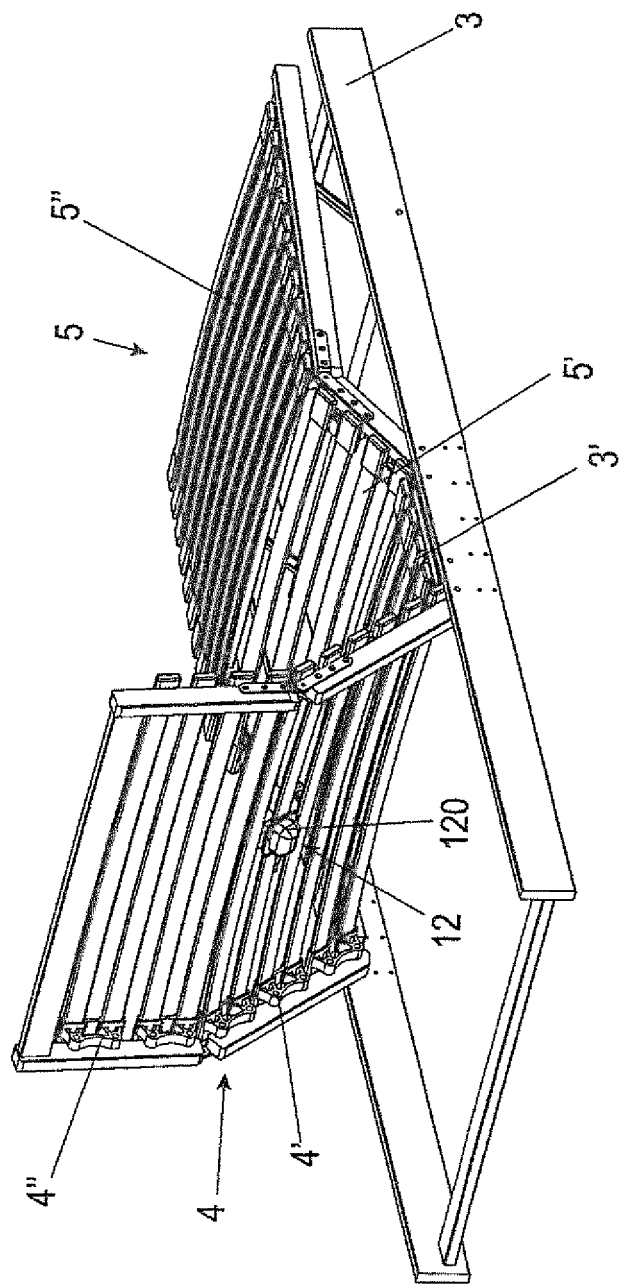
FIG. 10 shows an exemplary embodiment of a support element for sleeping furniture comprising a sensor.

FIG. 10 shows a further exemplary embodiment of a support element 3, which can be used in a bed (not shown here). In contrast to the support elements 3 comprising plate-shaped sections illustrated in FIGS. 4-7, the support element 3 illustrated in FIG. 10 has a frame construction which bears individual slats. Such a slatted frame can be used in conjunction with thinner mattresses than in the case of the above-mentioned box spring beds, since the slatted frame itself contributes a certain spring action. For reasons of comprehensibility, adjusting drives of the electric motor drive are not shown here. The support element 3 again comprises a back part 4, which has two sections 4' 4" pivotable relative to one another, a non-pivotable section 3', and a leg part 5 comprising the sections 5' and 5".

A sensor 12 is again arranged on the support element 3 at the back part 4, to record structure-borne sound and also airborne sound for further analysis. The sensor 12 is preferably again arranged in the middle in the transverse direction of the support element 3 and therefore of the bed. The sensor 12 is arranged in the lower to middle region of the back part 4 in the longitudinal direction.

Figure 11:
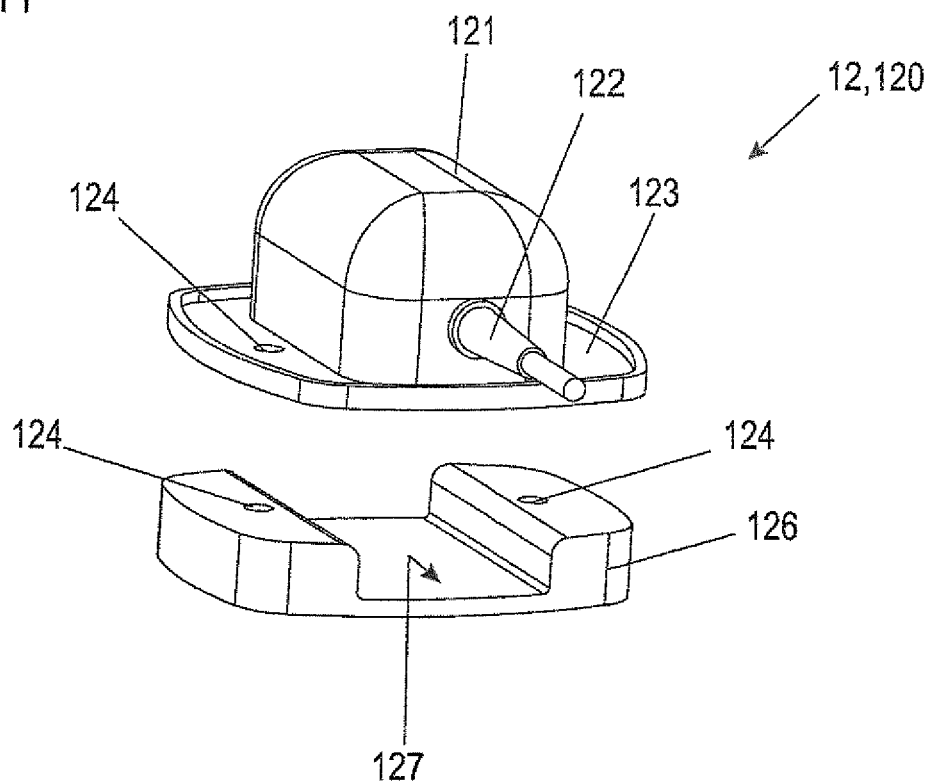
FIGS. 11 and 12 each show an isometric view of the sensor housing according to FIGS. 8 and 9 with an installation adapter.
Figure 12:
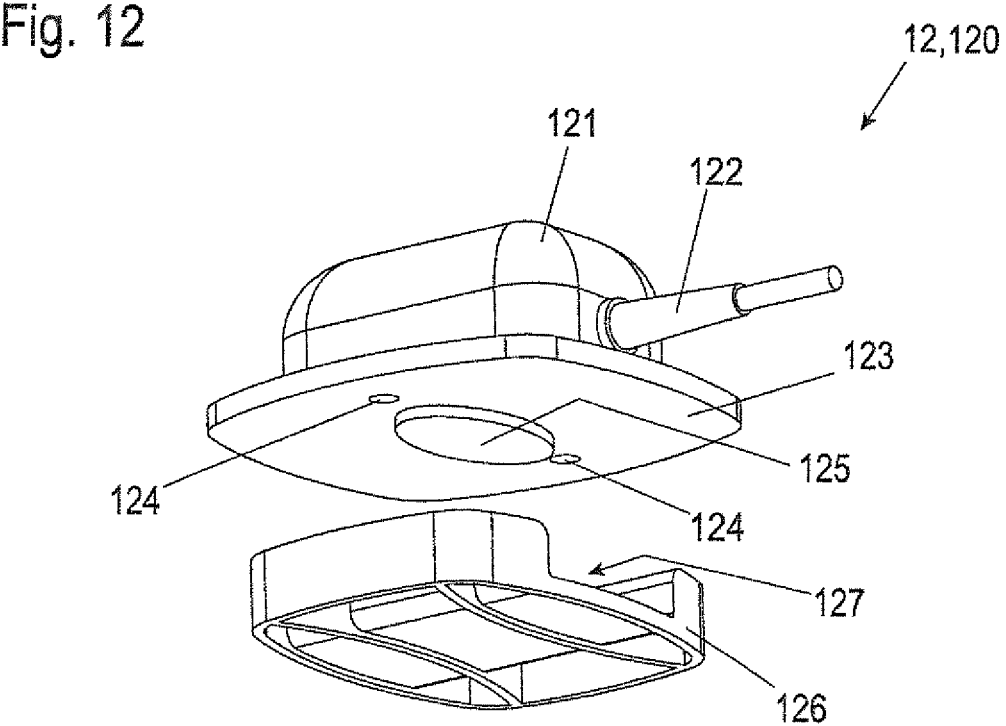

The sensor 12 used in the exemplary embodiment of FIG. 10 is illustrated in each of FIGS. 11 and 12 in an isometric illustration from various viewing directions.

The employed sensor 12 comprising sensor housing 120 corresponds here to that used in the exemplary embodiments of FIGS. 4 to 7, which is illustrated in greater detail in FIGS. 8 and 9. In principle, installation of the sensor housing 120 would also be possible in the slatted frame of the support element 3 according to FIG. 10.

Screwing the sensor housing 120 directly onto one of the slats is not advantageous, however, since the slats only have a relatively low thickness of approximately 8-12 mm and the risk exists that a screwed-in wood screw will penetrate through the upper side and destroy a mattress laid thereon and also cause a risk of injury. Moreover, a screwed-in wood screw could impair the stability of the slat.

Instead, the sensor 120 is fastened using an installation adapter 126 on one of the slats. The installation adapter 125 has a basic shape corresponding to the installation plate 123, through which a depression 127 extends, into which the slat of the slatted frame is inserted. The depth of the depression 127 is selected so that the slat, upon screwing of the installation plate 123 onto the installation adapter 126, is clamped between the two and the protrusion 125 on the lower side of the sensor housing 120 is pressed solidly against the corresponding slat.

The installation adapter 126 enables the sensor 12 in the housing 120 to be employed both for a use with plate-shaped support elements and also with a slatted frame as the support element. For slatted frames having slats of different widths and/or thicknesses, differently dimensioned installation adapters 126 can be provided.

The bed 1 illustrated in each of the exemplary embodiments of this application is a single bed. It is to be noted that a furniture drive according to the application comprising the sensor 12 can also be used if two or more beds 1 according to the above-mentioned embodiments are connected to one another to form a bedstead or if multiple support elements are accommodated adjacent to one another in a base element. The bed has multiple, preferably two middle non-pivotable sections 3' in the latter case, a corresponding number of pivotable back parts 4, and a corresponding number of leg parts 5. A mattress is typically assigned to each person.

Separate adjusting drives, which are electrically coupled, can be provided for each single bed or each support element. In the case of single beds or support elements which are mechanically connected to one another, sound decoupling elements can be provided, which enable the mechanical connection of two single beds or support elements, but at the same time damp or strongly reduce the structure-borne sound transmittable through the connection.

What is claimed is:

1. A sleeping or reclining furniture, in particular a bed, comprising:

an electric motor furniture drive including a plurality of adjusting motors for electromotive movement of a furniture component in relation to another furniture component;

a manual operation unit for operating the adjusting motors;

a fitting element coupling at least one of the adjusting motors to a back part of the sleeping or reclining furniture at a plurality of fastening points;

a sensor fastened on the back part between the plurality of the fastening points and configured to detect vibration and/or sound; and an analyzing unit connected to the sensor and configured to process and analyze a signal generated by the sensor and to detect a physiological parameter of a person using the sleeping or reclining furniture.

2. The sleeping or reclining furniture of claim 1, wherein the sensor is fastened in a lower half and in particular in a lower third of the back part of the sleeping or reclining furniture.

3. The sleeping or reclining furniture of claim 1, further comprising a control unit configured to control the adjusting motors, said analyzing unit being coupled to the control unit or integrated into the control unit.

4. The sleeping or reclining furniture of claim 1, wherein the sensor includes a piezoelectrically or electromagnetically or electromechanically operating sound and/or vibration pickup.

5. The sleeping or reclining furniture of claim 1, wherein the detected physiological parameter is a heart rate, a respiratory rate, and/or a movement state of the person.

6. The sleeping or reclining furniture of claim 1, wherein the analyzing unit includes a filter, in particular a low-pass filter or a bandpass filter for signal processing.

7. The sleeping or reclining furniture of claim 1, wherein the analyzing unit includes a storage unit for storing a time curve of the physiological parameters.

8. The sleeping or reclining furniture of claim 1, wherein the analyzing unit includes a monitoring device for comparing the physiological parameter to a predefined limiting value.

9. The sleeping or reclining furniture of claim 1, wherein the analyzing unit includes a transmitting unit for transmitting the physiological parameter to a mobile device.

10. The sleeping or reclining furniture of claim 9, wherein the transmitting unit is configured for wireless transmission of the physiological parameter to the mobile device, in particular via a WLAN or Bluetooth transmission link.

11. The sleeping or reclining furniture of claim 9, wherein the mobile device includes a monitoring device for comparing the physiological parameter to a predefined limiting value.

12. The sleeping or reclining furniture of claim 9, wherein the mobile device represents the manual operation unit.

13. The sleeping or reclining furniture of claim 1, wherein the analyzing unit is configured to detect and analyze vibrations which occur upon actuation of one or more of the adjusting motors.

14. The sleeping or reclining furniture of claim 1, wherein the analyzing unit is configured to ascertain a malfunction and/or an overload and/or a nonload of one or more of the adjusting motors in operation.

15. The sleeping or reclining furniture of cam 1, wherein the sensor includes a sensor housing having an installation surface which is formed with a protrusion, said sensor including a sound and/or vibration pickup which is arranged in an interior of the sensor housing in a region of the protrusion.

16. The sleeping or reclining furniture of claim 15, further comprising an installation adapter connected to the sensor housing to enclose a slat of a slatted frame for installation of the sensor on the slat.

* * * * *